(12) United States Patent
Smith et al.

(10) Patent No.: US 12,053,563 B1
(45) Date of Patent: Aug. 6, 2024

(54) CARRIER FOR FRAGRANCES

(71) Applicant: Rimports, LLC, Provo, UT (US)

(72) Inventors: Russell J. Smith, Saratoga Springs, UT (US); Clark Kalmar, Saratoga Springs, UT (US)

(73) Assignee: Rimports, LLC, Provo, UT (US)

( * ) Notice: Subject to any disclaimer, the term of this patent is extended or adjusted under 35 U.S.C. 154(b) by 0 days.

(21) Appl. No.: 17/342,473

(22) Filed: Jun. 8, 2021

Related U.S. Application Data

(60) Provisional application No. 63/036,260, filed on Jun. 8, 2020.

(51) Int. Cl.
  *A61L 9/04* (2006.01)
  *A61L 9/02* (2006.01)
  *C11B 9/00* (2006.01)

(52) U.S. Cl.
  CPC .................. *A61L 9/042* (2013.01); *A61L 9/02* (2013.01); *C11B 9/00* (2013.01)

(58) Field of Classification Search
  CPC ........................................................ C11B 9/00
  See application file for complete search history.

(56) References Cited

U.S. PATENT DOCUMENTS

2010/0209378 A1* 8/2010 Flachsmann .............. A61L 9/01
  568/822

* cited by examiner

*Primary Examiner* — Jessica Whiteley
(74) *Attorney, Agent, or Firm* — DENTONS Durham Jones Pinegar

(57) ABSTRACT

Chemical carriers for fragrances include components in proportions that enable a rate of diffusion or volatilization of at least one fragrance to be tailored. Such a fragrance carrier may include isopropyl myristate (IPM), 3-methyoxy-3-methyl-1-butanol (MMB), and cyclomethicone. The fragrance carrier may enable a fragrance to be delivered by a variety of different dispensers. Methods for optimizing the rates of diffusion or volatilization and other characteristics of fragrances using such a fragrance carrier are also disclosed.

20 Claims, No Drawings

CARRIER FOR FRAGRANCES

CROSS-REFERENCE TO RELATED APPLICATION

A claim for priority to the Jun. 8, 2020 filing date of U.S. Provisional Patent Application No. 63/036,260, titled CARRIER FOR FRAGRANCES ("the '260 Provisional Application") is hereby made pursuant to 35 U.S.C. § 119(e). The entire disclosure of the '260 Provisional Application is hereby incorporated herein.

TECHNICAL FIELD

This disclosure relates generally to chemical carriers for fragrances and, more specifically, to chemical carriers that include components that are included in proportions that enable a rate of diffusion of at least one fragrance to be tailored. Even more specifically, chemical carriers that include isopropyl myristate (IPM), 3-methyoxy-3-methyl-1-butanol (MMB), and cyclomethicone are disclosed. The disclosed carriers may enable a fragrance to be used for a variety of different purposes. Methods for optimizing the rates of diffusion and other characteristics of fragrances using such a chemical carrier are also disclosed.

RELATED ART

Many fragrances are formulated for a specific use; they cannot be used for other purposes. As an example, a fragrance that has been formulated for delivery in a particular manner may not be suitable for delivery in other ways. In a more specific example, a fragrance that has been formulated to provide a particular scent profile when used with a volatilizing diffuser may not provide the same scent profile when used in other ways; for example, with a more passive diffuser (e.g., a ceramic diffuser, etc.). Consequently, several different fragrance formulations are typically required to enable the same fragrance profile to be delivered by different types of devices, creating inefficiencies in the development, manufacture, and warehousing of fragrances.

Conventional fragrance formulations are typically harsh. When misused, such as by delivering them with a device or technique for which they have not been formulated, their delivery may not be optimized, which may increase the likelihood that they will cause damage. For example, when many conventionally formulated fragrances are not adequately dispersed or they leak or spill, the harsh solvents that are used in them may damage (e.g., stain, ruin finishes, etc.) of the surfaces (e.g., furniture, floors, etc.) they contact. Even when used properly, the harsh solvents that are used in many conventionally formulated fragrances may eventually damage the equipment (e.g., diffusers, etc.) used to disperse them, as well as objects (e.g., furniture, walls, floors, etc.) in the environments in which they are used.

SUMMARY

A chemical carrier for a fragrance may also be referred to herein as a "carrier" for the sake of simplicity. A carrier may include isopropyl myristate (IPM), 3-methoxy-3-methyl-1-butanol (MMB), and cyclomethicone. The IPM, the MMB, and the cyclomethicone may be included in the carrier in amounts or proportions that, when combined with one or more fragrance notes (i.e., the different scents that make up a fragrance, or the ingredients of a fragrance) can be delivered in a manner that provides desired rates of volatilization and/or diffusion.

The carrier may be formulated for use with a single fragrance or with any of a variety of different fragrances. The carrier may be formulated for use with a fragrance that includes one or more essential oils. The carrier may be formulated for use with a fragrance that includes one or more fragrance oils, which may include or consist of synthesized fragrances. The carrier may be formulated for use with a combination of different fragrances; i.e., with a fragrance that includes a combination of essential oil(s) and fragrance oil(s).

In some embodiments, a formulation of the chemical carrier may enable a fragrance to be used in a variety of different ways. Without limitation, the chemical carrier may enable a fragrance to be dispensed with a variety of different types of dispensers (e.g., volatilizing diffusers, passive diffusers, heated fragrance dispensers, warmers, etc.).

A formulation of the carrier may minimize a volatility, or a flash point (i.e., the ignition temperature), of an optimized fragrance of which the carrier is a part.

A formulation of the carrier may minimize a harshness of an optimized fragrance to surfaces, materials, and people and their pets with whom the optimized fragrance comes into contact. The surfaces and materials in question include materials that will be exposed to (e.g., contacted by, etc.) the optimized fragrance as it is properly used (e.g., the surfaces of a fragrance dispenser, etc.), the people and pets who will be exposed to the optimized fragrance or, more specifically, their skin, mucous membranes, eyes, etc., and surfaces the optimized fragrance may unintentionally contact, such as by way of leaks or spills (e.g., clothing, furniture surfaces, flooring surfaces, etc.).

In this context, "harshness" and similar terms may refer to the relative ability of the carrier to cause damage to surfaces, materials, and tissues it contacts. Such damage may include a change in appearance of a surface, such as by discoloring or staining the surface. Such damage may include dissolving, etching, or chemically reacting with other materials. Thus, harsh fragrances may discolor, stain, dissolve, etch, or chemically react with such other materials. Fragrances whose harshness has been minimized may not cause noticeable discoloration, staining, dissolution, etching, chemical reactions with such other materials, or other types of damage that may be caused by a harsh fragrance. "Harshness" and similar terms may also refer to the toxicity, causticity, and/or irritability of an optimized fragrance, with harsh fragrances being toxic, caustic, and/or irritating and fragrances whose harshness has been minimized lacking toxicity, causticity, or irritability.

In another aspect, an optimized fragrance may include a fragrance and a carrier for the fragrance. The fragrance may comprise one or more essential oils, one or more fragrance oils, or a combination of one or more essential oils and one or more fragrance oils. The carrier may include IPM, MMB, and cyclomethicone. The fragrance, the IPM, the MMB, and the cyclomethicone may be included in amounts or proportions that provide fragrance notes of the fragrance at a desired concentration or strength and with a desired rate of diffusion or volatilization.

Use of the carrier with a desired fragrance or combination of fragrances may enable the fragrance or fragrances to be used in a variety of different ways. For example, the carrier may enable the fragrance or fragrances to be used with any of a variety of different types of dispensers (e.g., any combination of volatilizing diffusers, passive diffusers, heated dispensers, warmers, etc.).

According to another aspect, methods for formulating optimized fragrances are within the scope of this disclosure. Such a method may include determining a base amount or proportion of IPM to be used with a base amount or proportion of a fragrance (i.e., a single fragrance, a combination of fragrances, etc.) to provide a desired concentration, or strength, of the fragrance. The extent to which the fragrance diffuses from the IPM and, optionally, from a diluent (e.g., water, an alcohol, another solvent, a combination of solvents, etc.) may then be determined. In addition, amounts or proportions of MMB and cyclomethicone that may be added to the fragrance and the IPM to provide the resulting optimized fragrance with a target rate of diffusion may then be determined. The target rate of diffusion may be greater than a rate of diffusion of the fragrance itself, greater than a rate of diffusion of the fragrance in the IPM, or slower than a rate of diffusion of the fragrance itself. Once blended, the fragrance, the IPM, the MMB, and the cyclomethicone define an optimized fragrance.

Other aspects of the disclosed subject matter, as well as features and advantages of various aspects of the disclosed subject matter, should become apparent to those of ordinary skill in the art through the preceding disclosure, the ensuing description, and the appended claims.

DETAILED DESCRIPTION

A carrier according to this disclosure is formulated to be used with a one or more fragrant oils to provide an optimized fragrance, which may be delivered by a plurality of different means. In some embodiments, the fragrant oil(s) and the carrier may be combined in a manner that enables the resulting optimized fragrance to be delivered by any of a variety of different techniques and/or with any of a variety of different delivery devices. Such a carrier may include IPM, MMB, and cyclomethicone.

IPM is a fatty acid ester with a chemical formula of $C_{17}H_{34}O_2$ and the following chemical structure:

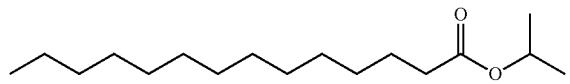 [SMILES: CCCCCCCCCCCCCC(=O)OC(C)C]

It is also known by a variety of other names, including propan-2-yl tetradecanoate, tetradecanoic acid, 1-methylethyl ester, myristic acid isopropyl ester. IPM is a polar emollient, meaning that it protects, moisturizes, and lubricates skin. Thus, IPM has been used conventionally as a moisturizer and in topical medical preparations to facilitate the absorption of other components into skin.

MMB is an alcohol-based solvent with the chemical formula $C_6H_{14}O_2$ and the following chemical structure:

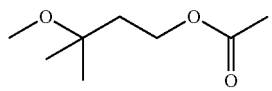

It is also known as 3-Methoxy-3-methylbutan-1-ol, 3-Methoxy-3-methylbutanol, 3-Methyl-3-methoxybutanol, 3-mercaptopropanoic acid methyl ester, methoxymethylbutanol. MMB has been used as a solvent for a variety of substances, including fragrances. It has low toxicity, is biodegradable, and has a weak odor.

Cyclomethicone is an organosilicon compound with the chemical formulas $C_{10}H_{30}O_5Si_5$ and $[(CH_3)_2SiO]_5$. It has the following chemical formula:

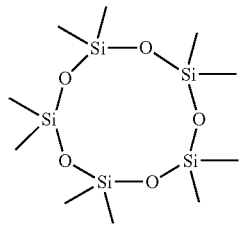

Cyclomethicone is known by a variety of names, including D5, decamethylcyclopentasiloxane, decamethyl-1,3,5,7,9,2, 4,6,8,10-pentaoxapentasilecane, cyclopentamethicone, cyclic dimethylsiloxane pentamer, and 2,2,4,4,6,6,8,8,10, 10-decamethylcyclopentasiloxane. It is an emollient and, thus, its use in cosmetics is common. Cyclomethicone is odorless, colorless, and slightly volatile.

The IPM, the MMB, and the cyclomethicone may be included in the carrier in amounts or proportions that provide fragrance notes of the fragrance with a desired rate of diffusion or volatilization. In some embodiments, the IPM may comprise about 92.5% to about 99% of a weight of the carrier. The MMB may comprise about 0.5% to about 5% of a weight of the carrier. The cyclomethicone may comprise about 0.5% to about 2.5% of a weight of the carrier. In a specific embodiment, the IPM may comprise about 97% of a weight of the carrier, the MMB may comprise about 2% of the weight of the carrier, and the cyclomethicone may comprise about 1% of the weight of the carrier.

The carrier may be combined with a fragrance to provide an optimized fragrance. The carrier may include IPM, MMB, and cyclomethicone. Optionally, the optimized fragrance may include a diluent. By way of non-limiting example, water, alcohol (e.g., isopropyl alcohol, etc.), another suitable solvent, or a combination of solvents may be used as a diluent of an optimized fragrance.

The fragrance may comprise one or more essential oils, one or more fragrance oils, or a combination of one or more essential oils and one or more fragrance oils. Each essential oil or fragrance oil may include a single fragrance note or a plurality of fragrance notes.

The IPM, the MMB, the cyclomethicone, and the fragrance may be included in amounts or proportions that deliver fragrance notes of the fragrance at a desired concentration or strength and with a desired rate of diffusion or volatilization. The carrier and the optimized fragrance may also be formulated in a manner that enables it to be delivered in a variety of different ways. For example, the carrier of the optimized fragrance may enable the optimized fragrance to be delivered with any of a variety of different types of dispensers (e.g., any combination of volatilizing diffusers, passive diffusers, heated dispensers, warmers, etc.). Examples of proportions of the IPM, the MMB, and the cylcomethicone have been provided above.

An optimized fragrance may include about 5% to about 25% of a weight of a fragrance. The IPM may comprise about 67.5% to about 94% of a weight of the optimized fragrance. The MMB may comprise about 0.5% to about 5% of a weight of the optimized fragrance. The cyclomethicone may comprise about 0.5% to about 2.5% of a weight of the optimized fragrance. Optionally, the optimized fragrance may include a diluent. In a specific embodiment, the fragrance may comprise about 20% of the weight of the optimized fragrance, the IPM may comprise about 77% of a weight of the optimized fragrance, the MMB may comprise about 2% of the weight of the optimized fragrance, and the cyclomethicone may comprise about 1% of the weight of the optimized fragrance.

A method for formulating an optimized fragrance includes identifying a fragrance note or a combination of fragrance notes to be included in the optimized fragrance. In embodiments where a plurality of fragrance notes are used, they may be included in a single fragrance oil or essential oil or in a combination of fragrance and/or essential oils.

A base amount or proportion of the IPM may then be determined. An amount or proportion of the fragrance to be added to the base amount or proportion of the IPM may then be determined. The amount or proportion of the fragrance may be based on a desired concentration, or strength, of the fragrance and/or a desired rate at which the fragrance diffuses or volatilizes from the IPM.

In addition, amounts or proportions of MMB, cyclomethicone, and any optional diluent to be added to the fragrance and the IPM may also be determined. The amounts or proportions of MMB, cyclometicone, and any optional diluent may be determined in conjunction with determining the amount of IPM to be included in the optimized fragrance to define an optimized fragrance with a desired concentration, or strength, of the fragrance and/or target rate of diffusion or volatilization. The target rate of diffusion or volatilization may be greater than a rate of diffusion or volatilization of the fragrance itself, greater than a rate of diffusion or volatilization of the fragrance in the IPM, or slower than a rate of diffusion or volatilization of the fragrance itself. Once blended, the fragrance, the IPM, the MMB, the cyclomethicone, and any optional diluent define an optimized fragrance.

Such a method may be conducted by a manufacturer, who may select the specific amounts or proportions of the ingredients to formulate and make an optimized fragrance. Alternatively, the carrier may be sold to a consumer, who may chose their own fragrance of combination of fragrances and combine the fragrance or combination of fragrances with the carrier (e.g., in proportions identified by the source of the carrier, etc.) to provide a custom optimized fragrance.

Although the preceding disclosure provides many specifics, these should not be construed as limiting the scope of any of the claims that follow, but merely as providing illustrations of some embodiments of elements and features of the disclosed subject matter. Other embodiments of the disclosed subject matter, and of their elements and features, may be devised which do not depart from the spirit or scope of any of the claims. Features from different embodiments may be employed in combination. Accordingly, the scope of each claim is limited only by its plain language and the legal equivalents thereto.

What is claimed:

1. A carrier for a fragrance, comprising:
isopropyl myristate (IPM);
3-methoxy-3-methyl-1-butanol (MMB); and
cyclomethicone,
the IPM, the MMB, and the cyclomethicone being precombined in amounts that provide fragrance notes of any fragrance of a plurality of different fragrances with a desired rate of diffusion or volatilization.

2. The carrier of claim 1, wherein the MMB comprises about 0.5% to about 5% of a weight of the carrier.

3. The carrier of claim 1, wherein the cyclomethicone comprises about 0.5% to about 2.5% of a weight of the carrier.

4. The carrier of claim 1, wherein the IPM comprises about 92.5% to about 99% of a weight of the carrier.

5. The carrier of claim 1, wherein:
the MMB comprises about 0.5% to about 5% of a weight of the carrier;
the cyclomethicone comprises about 0.5% to about 2.5 of the weight of the carrier; and
the IPM comprises about 92.5% to about 99% of the weight of the carrier.

6. The carrier of claim 1, formulated to minimize a volatility of any fragrance of the plurality of different fragrances.

7. The carrier of claim 1, formulated to minimize damage caused by any fragrance of the plurality of different fragrances.

8. A system for customizing a fragrance, the system comprising:
a plurality of fragrances; and
a carrier for any fragrance selected from the plurality of fragrances, the carrier including:
isopropyl myristate (IPM);
3-methoxy-3-methyl-1-butanol (MMB); and
cyclomethicone,
the IPM, the MMB, and the cyclomethicone being precombined with each other in amounts that will provide one or more fragrance notes of any fragrance selected from the plurality of fragrances with a desired rate of diffusion or volatilization.

9. The system of claim 8, wherein each fragrance of the plurality of fragrances comprises at least one essential oil.

10. The system of claim 8, wherein each fragrance of the plurality of fragrances comprises about 5% to about 25% of a weight of a combination of the fragrance with the carrier.

11. The system of claim 10, wherein the carrier comprises about 67.5% to about 94% of the weight of the combination of the fragrance with the carrier.

12. The system of claim 11, wherein the MMB comprises about 0.5% to about 5% of the weight of the combination of the fragrance with the carrier.

13. The system of claim 12, wherein the cyclomethicone comprises about 0.5% to about 2.5% of the weight of the combination of the fragrance with the carrier.

14. The system of claim 8, formulated to be dispersed by a variety of different types of dispensers.

15. The system of claim 8, formulated to minimize damage caused by each fragrance of the plurality of fragrances.

16. A method for optimizing a fragrance formulation, comprising:
selecting at least one fragrance from a plurality of fragrances comprising one or more essential oils and one or more fragrance oils;
determining an amount of the at least one fragrance of the plurality of fragrances to be added to a precombined carrier including:
a base amount of isopropyl myristate (IPM); a base amount of 3-methoxy-3-methyl-1-butanol (MMB); and
a base amount of cyclomethicone,
the base amount of 3-methoxy-3-methyl-1-butanol (MBB) and the base amount of cyclomethicone sufficient to increase a diffusion rate of the at least one fragrance to a target diffusion rate when diluted in the base amount of IPM.

17. The method of claim 16, wherein selecting the at least one fragrance comprises selecting at least one essential oil.

18. The method of claim 16, wherein selecting the at least one fragrance comprises selecting a combination of fragrances.

19. The method of claim 16, wherein determining the amount of the at least one fragrance to be added to the precombined carrier comprises determining amounts of the at least one fragrance and the precombined carrier that will minimize a volatility and/or a harshness of a resulting fragrance.

20. The method of claim 16, wherein determining the amount of the at least one fragrance to be added to the precombined carrier comprises determining amounts of the at least one fragrance and the precombined carrier that will optimize a safety of a resulting fragrance.

\* \* \* \* \*